United States Patent [19]

Gaenzler et al.

[11] 4,113,762

[45] Sep. 12, 1978

[54] METHOD OF MAKING CARBONIC ACID ESTERS

[75] Inventors: Wolfgang Gaenzler, Darmstadt-Arheilgen; Klaus Kabs, Seeheim; Güenter Schröeder, Ober-Ramstadt, all of Fed. Rep. of Germany

[73] Assignee: Rohm GmbH, Darmstadt, Fed. Rep. of Germany

[21] Appl. No.: 827,771

[22] Filed: Aug. 25, 1977

Related U.S. Application Data

[63] Continuation-in-part of Ser. No. 678,698, Apr. 20, 1976, abandoned.

[30] Foreign Application Priority Data

May 9, 1975 [DE] Fed. Rep. of Germany ....... 2520708

[51] Int. Cl.² ............................................. C07C 68/00
[52] U.S. Cl. ................................................... 260/463
[58] Field of Search .......................................... 260/463

[56] References Cited

U.S. PATENT DOCUMENTS

| | | | |
|---|---|---|---|
| 3,625,995 | 12/1971 | Brattesani | 260/463 |
| 3,846,468 | 11/1974 | Perrotti et al. | 260/463 |
| 3,952,045 | 4/1976 | Gaenzler et al. | 260/463 |
| 3,980,690 | 9/1976 | Cipriani et al. | 260/463 |

FOREIGN PATENT DOCUMENTS

| | | |
|---|---|---|
| 2,057,162 | 6/1971 | Fed. Rep. of Germany. |
| 2,334,736 | 4/1975 | Fed. Rep. of Germany ........... 260/463 |
| 2,431,330 | 1/1976 | Fed. Rep. of Germany ........... 260/463 |
| 7,011,129 | 4/1970 | Japan ....................................... 260/463 |

OTHER PUBLICATIONS

Nefedov, B. K. et al., Izv. Akad. Nauk SSSR, Ser. Khim, 1973, (4), 804–806.

*Primary Examiner*—Lewis Gotts
*Assistant Examiner*—Molly C. Eakin
*Attorney, Agent, or Firm*—Curtis, Morris & Safford

[57] ABSTRACT

A method for making a carbonic acid ester of the formula

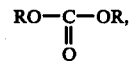

wherein R is —CH$_3$, —C$_2$H$_5$, or —C$_3$H$_7$, which comprises reacting the corresponding alcohol, ROH, with carbon monoxide and oxygen, under pressure and at elevated temperature, in the presence of a copper-containing catalyst, said catalyst being a complex formed between copper-I-chloride and vanadium trichloride, chromium trichloride, iron trichloride, cobalt-II-chloride, aluminum trichloride, or silicon tetrachloride.

3 Claims, No Drawings

METHOD OF MAKING CARBONIC ACID ESTERS

This application is a continuation-in-part of application Ser. No. 678,698 filed Apr. 20, 1976, now abandoned.

The present invention relates to a method of making carbonic acid esters.

Carbonic acid esters are valuable products finding use either as solvents or as starting products for the preparation of polycarbonates. By the transesterification of carbonic acid esters of the formula

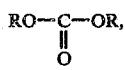

in which R is alkyl, aralkyl, or cycloalkyl, with glycols or diphenols, products are formed from which technically-significant polycarbonate resins can be formed by polycondensation. Trans-esterification of a carbonic acid ester of the aforementioned formula with 2,2-bis(4-hydroxy-phenyl)-propane (Bisphenol A), leads to important polycarbonate resins.

Carbonic acid esters are prepared either from phosgene and alcohols or by the reaction of an alcohol with carbon monoxide and oxygen in the presence of a catalyst. The present invention concerns a particularly advantageous method for carrying out the latter process. According to the method of the invention, carbonic acid esters of methyl-, ethyl-, propyl-, or isopropyl-alcohol are prepared by the reaction of these alcohols with carbon monoxide and oxygen in the presence of a copper-containing catalyst, under pressure and at elevated temperature. The heart of the invention lies in the use of particularly effective copper catalysts.

German patent publication DOS No. 2,110,194 discloses that the aforementioned process is favorably catalytically influenced by compounds of a metal of the IB group (copper, silver, or gold), or of the IIB group (zinc, cadmium, and mercury), or of group VIII (for example, iron, cobalt, and nickel) of the Periodic Table. As is evident from the Examples of this publication, which are without exception carried out with copper compounds, complexes of this metal evidently have a particular significance. In agreement with this finding is the proposal to carry out the same process in the presence of a catalyst system formed from a copper salt, a halide, and a triallyl phosphine oxide or an organic phosphite, phosphate, or phosphonate.

It has now been found that easily-prepared copper complexes influence the formation of carbonic acid esters from the aforementioned "lower" alcohols, carbon monoxide, and oxygen, in a particularly advantageous manner. In particular, the complex compounds are formed by the reaction of copper-I-chloride with vanadium chloride, chromium chloride, iron chloride, cobalt chloride, aluminum chloride, or silicon chloride. The preparation of the complex compounds in question can be described by an exemplary reference to the formation of the copper-aluminum tetrachloride complex, Cu (AlCl$_4$), known from DOS No. 2,057,162, which complex is most advantageous from the point of view of its catalytic efficacy. Thus, anhydrous aluminum chloride and copper-I-chloride are reacted in an aromatic hydrocarbon such as benzene, toluene, or xylene. Advantageously, the complex Cu(AlCl$_4$) is formed from stoichiometric amounts of the two metal chlorides. An excess of aluminum chloride is not desirable because of the instability of this compound. However, a "contamination" of the desired complex by excess copper-I-chloride also decreases the catalytic efficacy of the complex. The black complex dissolves in the aromatic hydrocarbon. This solution can be used per se for carrying out the process of the invention. When operating in concentrated solution, a portion of the complex precipitates and can be recovered from a solution by filtration or decantation. The portion dissolved in the solution can be recovered in solid form as a stable substance by evaporation of the hydrocarbon.

In the same fashion, copper-I-chloride can be reacted with vanadium trichloride, chromium trichloride, iron trichloride, cobalt-II-chloride, or silicon tetrachloride in order to form catalysts useful in the present invention. In this manner, the following complexes are formed: Cu(VCl$_4$), Cu(CrCl$_4$), Cu(FeCl$_4$), Cu(CoCl$_3$), and Cu(SiCl$_5$). Thus, the complexes to be used according to the process of the present invention can be represented by the general formula Cu(MeCl$_x$), wherein Me = V, Cr, Fe, Co, Al, or Si, and $x$ has a value equal to the valency of the metal, Me, present in the complex, + 1.

Although the aforementioned copper complexes are comparatively stable compounds, observations indicate that the catalyst partly undergoes a transformation during the reaction whereby, for example, a complex of the composition Cu[AlCl$_2$(OCH$_3$)$_2$] is formed from Cu(AlCl$_4$) in methanol, for example. Comparable changes can also occur with the remaining copper complexes. The course of ester formation over a long period of time is evidence that also these secondary products are catalytically effective. Thus, the protection sought by the present patent application encompasses also those complexes which are formed under the reaction conditions from Cu(VCl$_4$), Cu(CrCl$_4$), Cu(FeCl$_4$); Cu(CoCl$_3$), Cu(AlCl$_4$), and Cu(SiCl$_5$).

as is evident from the Examples herein, the method of the present invention proceeds at elevated temperature and under pressure. The fact that the oxygen employed can be used in the form of air represents an advantageous simplification from the point of view of economy and should, therefore, be specially mentioned. As is further evident from the Examples, carbonic acid esters are advantageously prepared according to the present invention in a pressure region between 10 and 200 atmospheres and at temperatures between 100° and 200° C. However, pressures or temperatures above or below these limits can also be employed and comprise embodiments intended to be protected herein. The process can be carried out discontinuously, or continuously using a pressure tube or pressurized coil.

The Chemical Engineers' Handbook, by John H. Perry, 3rd Edition, Mc Graw-Hill Book Company, Inc., New York (1950), on page 1234 incorporated herein by reference, defines "high pressure" as any pressure above a lower limit of about 50 atmospheres. By this criterion, then, the present reaction can be considered a high pressure reaction in view of the contemplated use of pressures up to or above 200 atmospheres.

The reference goes on to state:
"Five important factors should be kept continually in mind when selecting a metal for high-pressure service namely, (1) the working pressure, (2) the working temperature, (3) the size of the vessel, (4) the nature of the process with particular reference to the corrosive action of materials and (5) the stress conditions to be encountered, particularly whether static or dynamic. Steel is practically the only material available at reasonable cost with the necessary physical properties to withstand the mechanical stresses imposed by high pressures, though copper and bronzes are sometimes used on a small scale for pressure vessels and for tubing to convey fluids".

In consonance with these teachings, the reaction of the present invention is suitably carried out in steel vessels, for example of the type discussed in the ASME Boiler and Pressure Vessel Code Specification No. SA-240 (ASTM designation: A 240-54) entitled "Corrosion-Resisting Chromium and Chromium-Nickel Steel Plate, Sheet, and Strip for Fusion-Welded Unfired Pressure Vessels," incorporated herein by reference. A preferred steel of this kind is designated as V4A-steel, which is an austenitic chromium-nickel steel having 18% of Cr and 8% of Ni, Mo.

The catalysts employed in the method of the present invention have been found to be surprisingly less corrosive to the steels used in high pressure reactors than are other copper-containing catalysts known in the art, for example the complexes formed between copper chloride and certain phosphorus compounds known from Gaenzler U.S. Pat. No. 3,952,045 and the cupric ion used as an oxidant in Japanese Pat. No. 7,011,129 in reactions forming organic carbonates from alcohol and carbon monoxide.

The corrosiveness of materials such as these catalysts is conventionally tested by a "Total Immersion Test" described more in detail in the Chemical Engineers' Handbook, op. cit., pages 1458 et seq., incorporated herein by reference.

A better understanding of the present invention and of its many advantages will be had by referring to the following Examples, given by way of illustration.

EXAMPLE 1

Preparation of the Catalysts 1 mol of copper-I-chloride was stirred in toluene at room temperature for about 5 hours with 1 mol of a second anhydrous metal chloride ($AlCl_3$, $VCl_3$, $CrCl_3$, $FeCl_3$, $CoCl_2$, or $SiCl_4$). The filtered solution of the complex was evaporated on a rotary evaporator and the solid residue was employed as a catalyst without further treatment.

EXAMPLE 2

Preparation of a Carbonic Acid Ester 600 ml of alcohol, used both as a reaction medium and in part as a reagent, were introduced into a heatable 2-liter autoclave equipped with a glass liner together with 0.03 mol of, respectively, one of the aforementioned catalysts. After the introduction of 60 kg/cm² of carbon monoxide and from 40–60 kg/cm² of compressed air, the autoclave was heated to 170° C. The pressure sank during the reaction to about 20 kg/cm². After the decrease in pressure ceased, the autoclave was cooled, depressurized, and the reaction product was worked up by distillation. The carbonic acid ester formed was characterized by the usual analytical methods (nuclear resonance spectrum, infrared spectrum, and a gas chromatograph/mass spectrograph combination).

The following esters were prepared using the different copper complexes:

| Example | Catalyst (0.03 mol) | Alcohol | Dialkylcarbonate (g) |
|---|---|---|---|
| a) | $Cu(AlCl_4)$ | $CH_3OH$ | 31.6 |
| b) | $Cu(AlCl4)$ | $C_2H_5OH$ | 21.6 |
| c) | $Cu(AlCl_4)$ | $i-C_3H_7OH$ | 4.0 |
| d) | $Cu(VCl_4)$ | $CH_3OH$ | 16.0 |
| e) | $Cu(CrCl_4)$ | $CH_3OH$ | 18.5 |
| f) | $Cu(FeCl_4)$ | $CH_3OH$ | 13.4 |
| g) | $Cu(CoCl_3)$ | $CH_3OH$ | 13.6 |
| h) | $Cu(SiCl_5)$ | $CH_3OH$ | 16.4 |

Examples a) and b): $CO = 60$ kg/cm²; air = 60 kg/cm²
Examples c) –h): $CO = 60$ kg/cm²; air = 40 kg/cm²

What is claimed is:

1. A method for making a carbonic acid ester of the formula $$RO-\underset{\underset{O}{\|}}{C}-OR,$$

wherein R is $-CH_3$, $-C_2H_5$, or $-C_3H_7$, which comprises reacting the corresponding alcohol, ROH, with carbon monoxide and oxygen at a temperature between about 100° and 200° C. and at a pressure between about 10 and 200 atmospheres in the presence of a catalytic amount of a copper-containing catalyst, said catalyst consisting essentially of a complex each molar part of which is formed between one molar part of copper-I-chloride and one molar part of a member selected from the group consisting of vanadium trichloride, chromium trichloride, iron trichloride, cobalt-II-chloride, aluminum trichloride, and silicon tetrachloride.

2. A method as in claim 1 wherein said complex is $Cu(AlCl_4)$.

3. A method as in claim 1 wherein said oxygen is in the form of air.

* * * * *